(12) United States Patent
Yoneto et al.

(10) Patent No.: US 9,855,206 B2
(45) Date of Patent: Jan. 2, 2018

(54) HYALURONIC ACID GEL AND MANUFACTURING METHOD THEREOF

(71) Applicant: COSMED PHARMACEUTICAL CO., LTD., Kyoto, Kyoto (JP)

(72) Inventors: Kunio Yoneto, Takatsuki (JP); Junya Hasegawa, Kyoto (JP); Naoko Kondou, Kyoto (JP); Ying-shu Quan, Kyoto (JP); Fumio Kamiyama, Kyoto (JP)

(73) Assignee: COSMED PHARMACEUTICAL CO., LTD., Kyoto (JP)

( * ) Notice: Subject to any disclaimer, the term of this patent is extended or adjusted under 35 U.S.C. 154(b) by 0 days.

(21) Appl. No.: 14/436,463

(22) PCT Filed: Aug. 2, 2013

(86) PCT No.: PCT/JP2013/071003
§ 371 (c)(1),
(2) Date: Apr. 16, 2015

(87) PCT Pub. No.: WO2014/061332
PCT Pub. Date: Apr. 24, 2014

(65) Prior Publication Data
US 2015/0272850 A1  Oct. 1, 2015

(30) Foreign Application Priority Data

Oct. 17, 2012  (JP) .................. 2012-242203

(51) Int. Cl.
| | |
|---|---|
| *A61K 8/73* | (2006.01) |
| *C08J 3/075* | (2006.01) |
| *C08L 5/08* | (2006.01) |
| *A61Q 19/08* | (2006.01) |
| *A61K 8/04* | (2006.01) |
| *A61K 8/365* | (2006.01) |
| *A61Q 19/00* | (2006.01) |
| *A61K 8/34* | (2006.01) |
| *C08G 63/66* | (2006.01) |
| *A61K 8/02* | (2006.01) |
| *A61K 8/362* | (2006.01) |

(52) U.S. Cl.
CPC ............ *A61K 8/735* (2013.01); *A61K 8/0212* (2013.01); *A61K 8/0216* (2013.01); *A61K 8/042* (2013.01); *A61K 8/345* (2013.01); *A61K 8/362* (2013.01); *A61K 8/365* (2013.01); *A61Q 19/00* (2013.01); *A61Q 19/08* (2013.01); *C08G 63/66* (2013.01); *C08J 3/075* (2013.01); *C08L 5/08* (2013.01); *A61K 2800/22* (2013.01); *A61K 2800/242* (2013.01); *C08J 2305/08* (2013.01)

(58) Field of Classification Search
CPC ...... A61K 8/0216; A61K 8/042; A61K 8/365; A61K 8/735; A61K 8/362; A61K 8/73; A61Q 19/00; C08J 3/075
See application file for complete search history.

(56) References Cited

U.S. PATENT DOCUMENTS

| | | | | | |
|---|---|---|---|---|---|
| 5,879,711 | A | * | 3/1999 | Sequeira | A61K 9/0014 424/488 |
| 6,136,297 | A | * | 10/2000 | Sagel | A61K 8/0208 106/35 |
| 2006/0147393 | A1 | * | 7/2006 | Macchi | A61K 8/735 424/49 |
| 2009/0312282 | A1 | * | 12/2009 | Yoshida | A23L 1/056 514/54 |
| 2012/0309623 | A1 | * | 12/2012 | Ahn | C08J 3/126 504/187 |
| 2016/0081906 | A1 | | 3/2016 | Yoneto | |

FOREIGN PATENT DOCUMENTS

| | | |
|---|---|---|
| CN | 101450028 A | 6/2009 |
| CN | 102266273 A | 12/2011 |
| EP | 1 281 722 A1 | 2/2003 |
| EP | 1 818 344 A1 | 8/2007 |
| FR | 2 650 180 A1 | 2/1991 |
| GB | 2 235 204 A | 2/1991 |
| JP | 61-180705 A | 8/1986 |
| JP | 63-159452 A | 7/1988 |
| JP | 3-63209 A | 3/1991 |
| JP | 5-58881 A | 3/1993 |
| JP | 6-65048 A | 3/1994 |
| JP | 8-143604 A | 6/1996 |
| JP | 9-110680 A | 4/1997 |
| JP | 2000-273033 A | 10/2000 |
| JP | 3094074 B2 | 10/2000 |
| JP | 2001-64154 A | 3/2001 |
| JP | 2001-335427 A | 12/2001 |
| JP | 2002-212047 A | 7/2002 |

(Continued)

OTHER PUBLICATIONS

Kogan et al (Biotechnology Letters, 2007, vol. 29, pp. 17-25).*
International Search Report for the Application No. PCT/JP2013/071003 mailed Oct. 29, 2013.
Written Opinion of the International Searching Authority (PCT/ISA/237) for Application No. PCT/JP2013/071003 mailed Oct. 29, 2013.
Notification of the Third Party Observation (PCT/IB/345) for the Application No. PCT/JP2013/071003 from the International Bureau of WIPO mailed Oct. 1, 2014.
Written Opinion of the International Searching Authority (PCT/ISA/237) for Application No. PCT/JP2013/071003 mailed Oct. 29, 2013 (English Translation mailed Apr. 30, 2015).

(Continued)

*Primary Examiner* — Mark V Stevens
(74) *Attorney, Agent, or Firm* — Cheng Law Group, PLLC

(57) ABSTRACT

Provided is hyaluronic acid gel suitable for cosmetic and medical field.
The hyaluronic acid gel contains hyaluronic acid, polycarboxylic acid or oxycarbonic acid, and polyhydric alcohol. The hyaluronic acid gel is produced by drying moisture of an aqueous solution in which the hyaluronic acid, the polycarboxylic acid, and the polyhydric alcohol are uniformly dissolved to be an intended form.

21 Claims, No Drawings

(56) References Cited

FOREIGN PATENT DOCUMENTS

| | | |
|---|---|---|
| JP | 2002-338423 A | 11/2002 |
| JP | 2005-22980 A | 1/2005 |
| JP | 2005-60234 A | 3/2005 |
| JP | 2006-306843 A | 11/2006 |
| JP | 2007-512410 A | 5/2007 |
| JP | 2007-297460 A | 11/2007 |
| JP | 2009-102228 A | 5/2009 |
| JP | 2010-82401 A | 4/2010 |
| JP | 2010-130920 A | 6/2010 |
| JP | 2010-215553 A | 9/2010 |
| JP | 2013-223644 A | 10/2013 |
| WO | WO-97/04012 A1 | 2/1997 |
| WO | WO-01/57093 A1 | 8/2001 |
| WO | WO-2005/055924 A2 | 6/2005 |
| WO | WO-2006/051950 A1 | 5/2006 |
| WO | WO-2008/119456 A2 | 10/2008 |
| WO | WO-2015/002091 A1 | 1/2015 |

OTHER PUBLICATIONS

Supplementary European Search Report for the Application No. EP 13 84 7345 dated Apr. 21, 2016.
The First Office Action for the Application No. 201380052533.8 from The State Intellectual Property Office of the People's Republic of China dated Jun. 1, 2016.
Notification of Reasons for Refusal for the Application No. 2015446211 from Japan Patent Office dated Aug. 4, 2016.
Third Party Submission of Patents or Publications for the Application No. 2012-242203 from Japan Patent Office dated Aug. 28, 2015,.
Third Party Submission of Patents or Publications for the Application No. 2015-446211 from Japan Patent Office dated Nov. 16, 2015.

\* cited by examiner

HYALURONIC ACID GEL AND MANUFACTURING METHOD THEREOF

TECHNICAL FIELD

The present invention relates to hyaluronic acid gel and a manufacturing method thereof.

BACKGROUND ART

Hyaluronic acid is a linear polymeric polysaccharide binding to β-D-N-acetylglucosamine and β-D-glucuronic acid alternately. Hyaluronic acid is distributed in connective tissues of mammals and otherwise prepared by isolation and extraction from crest and umbilical cord of chicken, etc. or by fermentation using microorganisms such as *Streptococcus*.

In addition, since hyaluronic acid is contained in a human body, has excellent biocompatibility, and shows various medicinal effects primarily including moisture retaining action, it is attracting attention as a natural material in the medical and cosmetic fields. In addition, hyaluronic acid gel is excellent in handleability and very useful in the medical and cosmetic fields.

Although the hyaluronic acid gel is usually prepared by crosslinking hyaluronic acid through chemical modification (Patent Documents 1 to 3), the crosslinked hyaluronic acid chemically modified is not a natural hyaluronic acid itself. Also, although manufacturing methods for hyaluronic acid gel using acids are known (Patent Documents 4 and 5), they are unsuitable for manufacturing hyaluronic acid gel in a form of a gel sheet or the like which takes complex processes and is required for the medical and cosmetic fields. In addition, since such gel is poorly water-soluble, hyaluronic acid is not dissolved, and thus they are unsuitable as gel used in the cosmetic field aimed at actions of the hyaluronic acid on the skin for providing moisture and tension to the skin.

Recently, scientific effectiveness of skin heating as a countermeasure to wrinkles is known and attracting attention. As cosmetics for increasing a temperature of skin, cosmetics which generate heat by mixing a polyhydric alcohol such as glycerin with water to provide hyperthermic effects have already been known (Patent Documents 6 and 7). However, these cosmetics are to be heated by mixing a polyhydric alcohol-containing preparation with a water-containing preparation and then applied to skin in using, and thus the handling is complicated.

A cosmetic which makes skin absorb $CO_2$ gas to improve bloodstream is also known (Patent Document 8). However, use of this cosmetic is also complicated because the cosmetic is to be applied to the face while $CO_2$ gas is generated by mixing a carbonate-containing preparation with an acidic components-containing preparation in using.

PRIOR ART DOCUMENTS

Patent Documents

[Patent Document 1] JP-3094074A
[Patent Document 2] JP-H08143604A
[Patent Document 3] WO2006/051950
[Patent Document 4] JP-H0558881A
[Patent Document 5] WO2001/57093
[Patent Document 6] JP-2002338423A
[Patent Document 7] JP-2006306843A
[Patent Document 8] JP-2002338423A

SUMMARY OF INVENTION

Technical Problem

An object to be achieved by the present invention is to provide a cosmetic comprising hyaluronic acid gel which solves the above-mentioned conventional problems, is prepared by a simple process, has flexibility, elasticity and tensile strength required for cosmetics by exploiting excellent original properties of the hyaluronic acid, sufficiently fits the surface of the skin, and adheres tightly to the skin to provide moisture-rich effects on the skin. Furthermore, another object is to provide a cosmetic characterized in that, when the hyaluronic acid gel cosmetic is applied to skin and then the skin is massaged with water, the gel is rapidly dissolved, and the hyaluronic acid and the ingredients contained in the cosmetic are absorbed in the skin.

Furthermore, the other object to be achieved by the present invention is to provide a cosmetic which is applied to skin and shows high anti-wrinkle effects and cosmetic effects.

Solution to Problem

The hyaluronic acid gel according to the present invention made for solving the above-mentioned problems is characterized by containing hyaluronic acid, polycarboxylic acid or oxycarbonic acid, and polyhydric alcohol.

The hyaluronic acid gel according to the present invention rapidly dissolves by adding an appropriate amount of water or skin lotion.

The reason for the rapid dissolution is that the material is suitably selected.

Hyaluronic acid gel having the desired properties can be easily prepared by preparing an aqueous solution containing hyaluronic acid, polycarboxylic acid or oxycarbonic acid, and polyhydric alcohol, and drying its moisture.

A content of the polycarboxylic acid or oxycarbonic acid is preferably 10 to 400 pts. wt., more preferably 10 to 100 pts. wt. with respect to 100 pts. wt. of the hyaluronic acid. A content of the polyhydric alcohol is preferably 100 to 8000 pts. wt. with respect to 100 pts. wt. of the hyaluronic acid. Cosmetic valuable components may be contained in the ingredients.

The hyaluronic acid gel is characterized in that, when the gel is brought into contact with a large amount of water, the structure of the gel is broken and the hyaluronic acid dissolves. The hyaluronic acid gel in the present invention can reversibly become gelatinous and soluble. Thus, by applying the gel in a gelatinous state to skin and then massaging the skin with an appropriate amount of water, the hyaluronic acid gel is solubilized, and the hyaluronic acid and the valuable compounds can be effectively absorbed in the skin.

Characteristically, when the water-soluble hyaluronic acid gel is applied to skin, a large amount of the polyhydric alcohol contained in the gel is hydrated with water to generate heat, and it gives mild warm sensation to the skin and heals the skin.

The hyaluronic acid gel is shaped into a suitable sheet shape as a cosmetic such as a whole-face sheet and an eye sheet. A thickness of the sheet is preferably 30 µm to 1 mm. When the thickness of the sheet is smaller than 30 µm, its handling may be difficult because of low strength of the sheet, and the warm sensation in application to the skin may be lowered. When the thickness is 1 mm or more, the handling may also be difficult because of its heaviness.

The hyaluronic acid gel as a cosmetic is characterized in that, when the gel is brought into contact with a large amount of water, the structure of the gel is broken and the hyaluronic acid dissolves. The hyaluronic acid gel can reversibly become gelatinous and soluble. Thus, by applying the gel in a gelatinous state to skin and then massaging the skin with an appropriate amount of water, the hyaluronic acid gel is solubilized, and the hyaluronic acid and the valuable compounds can be effectively absorbed in the skin.

At this time, if the skin is massaged using water or skin lotion containing valuable components, the structure of the gel is broken and dissolves as a water-soluble hyaluronic acid while providing warm sensation. When water or skin lotion containing an appropriate amount of carbonate is used, the carbonate is oxidized to $CO_2$ gas and foams on the skin, because the hyaluronic acid gel is acidic due to the hyaluronic acid and the polyhydric alcohol. As the carbonate, sodium carbonate, sodium hydrogen carbonate, potassium carbonate, etc. may be used. Characteristically, the $CO_2$ gas generated on the skin surface is incorporated into the skin to enhance metabolism of the skin cells and activation of the skin, so that the cosmetic effects can be further increased.

In the present invention, the hyaluronic acid as a raw material may be either one extracted from animal tissues or one produced by fermentation. In addition, the hyaluronic acid may be a metal salt such as sodium salt, potassium salt, or the like.

In the present invention, a molecular weight of the hyaluronic acid as a raw material is preferably from about $5 \times 10^4$ to about $5 \times 10^6$ daltons. Note that the molecular weight in the present invention is represented by viscosity-average molecular weight. In this range, two kinds or more of hyaluronic acids having different molecular weights may be blended for use. In addition, a hyaluronic acid with a molecular weight within this range and a hyaluronic acid with a molecular weight smaller than this range may be blended for use. The dissolution rate of the gel can be accelerated by addition of low molecular weight water-soluble substances such as a low molecular weight hyaluronic acid (molecular weight: $2 \times 10^4$ or smaller), collagen and acetylglucosamine.

An amount of the hyaluronic acid used in the present invention in the gel is preferably from 0.1 wt % to 50 wt %. If the amount of the hyaluronic acid in the gel is less than 0.1 wt %, the gel softens, and gel having excellent elasticity may be hardly produced. On the other hand, if the amount is beyond 50 wt %, the gel hardens, the gel having excellent elasticity may be hardly produced, and adhesiveness to the skin may be poor.

The polycarboxylic acid used in the present invention is not particularly limited as long as it includes any polycarboxylic acid having two or more carboxylic acid groups in its molecule. The oxycarbonic acid is not particularly limited as long as it includes any oxycarbonic acid having a carboxylic acid group and a hydroxyl group in the molecule. For example, citric acid, lactic acid, tartaric acid, oxalic acid, etc. can be used. Particularly, citric acid and lactic acid are preferable. In addition, two kinds or more of polycarboxylic acids or oxycarbonic acids can be blended for use.

An amount of the polycarboxylic acid or oxycarbonic acid is preferably 10 pts. wt. or more, more preferably 20 to 100 pts. wt. with respect to 100 pts. wt. of the hyaluronic acid. When it is less than 10 pts. wt., gel having excellent elasticity may be hardly produced. On the other hand, when it is more than 100 pts. wt., acidity of the gel is unnecessarily increased, the gel may be hardly produced.

Polyhydric alcohol used in the present invention is not limited and may include glycerin, propylene glycol, polyethylene glycol, 1,3-butylene glycol, dipropylene glycol, sorbitol, etc. Among them, glycerin and propylene glycol are particularly preferable.

The amount of the polyhydric alcohol is preferably 100 pts. wt. or more, more preferably 200 to 8000 pts. wt. with respect to 100 pts. wt. of the hyaluronic acid. If the amount of the polyhydric alcohol is less than 100 pts. wt., gel having excellent elasticity may be hardly produced. On the other hand, if the amount is beyond 8000 pts. wt., the gel softens, and the gel having excellent elasticity may be hardly produced.

In the present invention, furthermore, at least one or more compounds selected from a group consisting of hydroxypropyl cellulose, polyvinylpyrrolidone, polyvinyl alcohol, carboxymethylcellulose, polyacrylic acid and polyethylene glycol may be included. In this case, the inclusion of the above water-soluble polymers leads to improvement of mechanical strength of the hyaluronic acid gel and increase of the viscosity of the aqueous solution, and thus is preferable for manufacture stability.

In the present invention, an appropriate amount of water can be contained in the hyaluronic acid gel for adjusting the hardness, as required.

In the hyaluronic acid gel and gel sheet of the present invention, active ingredients used for cosmetics and medicinal products can be blended to the extent that does not affect the purpose and effects of the present invention. Particularly, they are advantageous for application as cosmetics and quasi drugs. The compoundable active ingredients may include, for example, whitening components, anti-wrinkle components, anti-inflammatory components, blood circulation promoting components, antimicrobial components, anti-itching components, various vitamins and their derivatives, antioxidative components, pigments, fragrances, etc.

The whitening components include, but are not limited to, vitamin C derivatives such as ascorbic acid phosphate ester magnesium salt, ascorbic acid glucoside and salt and acyl derivative thereof, ethylascorbic acid and ascorbyl palmitate, α-arbutin, β-arbutin, kojic acid, placenta extract, cysteine, glutathione, ellagic acid, rucinol, tranexamic acid, baicalein, adenosine and sodium phosphate thereof, astaxanthin, deer horn shape *ganoderma lucidum*, oil-soluble licorice, lavender, lempuyang, burnet, resveratrol, *ganoderma lucidum*, extracts of them, components contained in tincture or them, etc., for example.

The moisturizing components include lactic acid, urea, sorbitol, amino acid, acetylglucosamin, etc.

The anti-wrinkle components include, but are not limited to, retinoid such as retinol, retinoic acid, retinol acetate and retinol palmitate, α-hydroxy acid such as citric acid, fruit acid, glycolic acid and lactic acid, α-hydroxyl acid cholesterol, rutin derivative, N-methylserine, elastin, collagen, sericin, *centella asiatica* extract, *scutellaria baicalensis* extract, etc.

The anti-inflammatory components include, but are not limited to, glycyrrhetinic acid, ghycyrrhetinic acid 2K, allantoin, epsilon-aminocaproic acid, azulene, shikonin, tranexamic acid, and *Coptis japonica*, licorice, Terminalia, yallow, tooth root, comfrey, aloe, Butcher Bloom, horse chestnut, peach leaf, loquat leaf, extracts of them, components contained in tincture or them, etc., for example.

The blood circulation promoting components include, but are not limited to, vitamin E, nicotinic acid, nicotinic acid amide, benzyl nicotinate, nicomol, caffeine, capsaicin, nonanoic acid vanillylamide, shogaol, gingerol, etc., for example.

The antimicrobial components include, but are not limited to, cationic surfactant such as isopropyl methylphenol, triclosan, triclocarban, trichloro-hydroxyphenol, halocarbon, benzalkonium chloride and benzethonium chloride, photosensitizer, zinc oxide, titanium oxide, chitin, chitosan, hinokiol, anise, etc., for example.

The anti-itching components include, but are not limited to, diphenhydramine hydrochloride, chlorpheniramine maleate, crotamiton, glycyrrhizin acid, menthol, camphor, rosemary oil, capsaicin, nonanoic acid vanillylamide, dibucaine, etc., for example.

The vitamins as oil-soluble vitamin include, but are not limited to, vitamin A oil, cod-liver oil, retinol acetate, retinol palmitate, retinol, dehydroretinol, vitamin $A_3$, retinoic acid, vitamin D, vitamin $D_2$ (ergocalciferol), vitamin $D_3$ (cholecalciferol), vitamin derivative, vitamin E (tocopherol), dl-α-tocopherol acetate, dl-α-tocopherol, tocopherol butyrate, tocopheryl nicotinate, nicotinic acid benzyl ester, natural vitamin E, vitamin K, vitamin U, etc., for example. In addition, the vitamins as water-soluble vitamin include vitamin $B_1$ (thiamin), vitamin $B_2$ (riboflavin tetrabutyrate), vitamin $B_6$ (fatty acid ester such as pyridoxine dicaprylate and pyridoxine dipalmitate), vitamin $B_{12}$ (cobalamin), vitamin $B_{13}$, vitamin $B_{14}$, vitamin $B_{15}$ (pangamic acid), folic acid, carnitine, thioctic acid, pantothenyl alcohol, pantothenyl ethyl ether, pantothenic acid, nicotinic acid, nicotinic-acid amide, choline, inositol, vitamin C (ascorbic acid), ascorbyl stearate, ascorbyl pantothenate, ascorbyl dipalmitate, vitamin H (biotin), vitamin P (hesperidin), Apprecier (APPS), etc.

The antioxidative components include, but are not limited to, polyphenols such as anthocyanin, catechin, green tea polyphenol and apple polyphenol, carotenoids such as ascorbic acid, sodium ascorbate, sodium sulfate ascorbate, β-carotene and astaxanthin, β-diketones such as tocopherols, tocopherol acetate, natural vitamin E, tocomonoenol, tocotrienol and curcumin, lignins such as sesamin and sesamolin, phenols such as eugenol, etc., for example.

Anti-allergic components include, but are not limited to, glycyrrhetinic acid derivative such as glycyrrhetinic acid and glycyrrhetinic acid 2K, licorice, chlorella, comfrey, moutan cortex, *Tilia cordata, Isodon japonicus*, sage, shiso, mugwort, extracts of them, components contained in tincture or them, etc., for example.

In the skin lotion used in the present invention, ingredients used for cosmetics and medicinal products can be blended to the extent that does not affect the purpose and effects of the present invention. Particularly, they are advantageous for application as cosmetics and quasi drugs. The compoundable ingredients may include, for example, whitening components, anti-wrinkle components, anti-inflammatory components, blood circulation promoting components, antimicrobial components, anti-itching components, various vitamins and their derivatives, antioxidative components, pigments, fragrances, etc.

In order to generate $CO_2$ gas by adding water or skin lotion to the hyaluronic acid gel and the gel of the present invention, it is preferable that water or the skin lotion is previously adjusted to around pH 6.5 to 7.5 by adding a carbonate such as sodium carbonate and sodium bicarbonate. When water or the skin lotion is applied on the hyaluronic acid gel sheet and the skin is massaged, the carbonate is reacted with the acid in the hyaluronic acid gel sheet to generate $CO_2$ gas. A concentration of the used carbonate in water or the skin lotion is preferably 2 to 20%, more preferably 3 to 7%. When it is lower than 2%, $CO_2$ gas is hardly generated, and when it is 20% or higher, the carbonate is not completely reacted and remains on the skin, and the skin texture may become worse.

In the present invention, the hyaluronic acid gel may be sheet-shaped.

Although the method for manufacturing the hyaluronic acid gel is not particularly limited in the present invention, a hyaluronic acid, a polycarboxylic acid or oxycarbonic acid and a polyhydric alcohol are uniformly dissolved in water, at least a part of the moisture is dried so as to be an intended form, and thereby the hyaluronic acid gel can be manufactured.

In addition, the manufacturing method for the hyaluronic acid according to the present invention may include a step of preparing an aqueous solution in which the hyaluronic acid, the polycarboxylic acid or oxycarbonic acid and the polyhydric alcohol are uniformly dissolved in water, and a step of producing the sheet-like hyaluronic acid gel by applying the aqueous solution on a film so that its thickness is uniform and drying it.

For example, respective aqueous solutions, each of which contains the hyaluronic acid, the polycarboxylic acid or oxycarbonic acid and the polyhydric alcohol, are stirred and homogenized by a propeller type rotary stirrer, for preparation. The prepared aqueous solution is applied on a polyethylene terephthalate film so that its thickness is uniform, and dried by hot air to produce the transparent sheet-like hyaluronic acid gel with a uniform thickness. In actual use, it is desirable that the sheet is cut and used as a circle, oval, comma-shaped and face-shaped sheet cosmetic.

Advantageous Effects of Invention

For the hyaluronic acid gel of the present invention, the original excellent properties of the hyaluronic acid are exploited. Hyaluronic acid gel which is not chemically crosslinked is water-soluble, and useful as a material used particularly for the cosmetic field. When the gel is applied on skin and the skin is massaged with a small amount of water or skin lotion, the hyaluronic acid and the ingredients penetrate into the skin, and even when the gel is subsequently rinsed with a large amount of water, the effects of the hyaluronic acid and the ingredients are sustained to provide a moisture sensation and smoothness to the skin. Furthermore, a warm sensation is provided to the skin, so that the skin texture becomes pleasant.

When the skin is massaged with water or skin lotion containing a carbonate, the carbonate ion is converted into $CO_2$ gas by acidic components in the hyaluronic acid gel, and penetrates into the skin. Even when the gel is subsequently rinsed with a large amount of water, the effects of the hyaluronic acid, the ingredients and $CO_2$ gas are sustained to provide a moisture sensation, smoothness and fluffy sensation to the skin.

DESCRIPTION OF EMBODIMENTS

Hereinafter, the present invention will be explained with reference to Examples, but the present invention is not originally limited to Examples.

(Manufacture of the Hyaluronic Acid Gel Sheet)

The hyaluronic acid gel sheets in Examples 1 to 29 and Comparative Examples 1 to 9 were produced according to the compounding ratios (weight ratio) described in Table 1 and Table 2 below. In Table 1 and Table 2, the molecular weights of the used hyaluronic acid are described below the columns of the hyaluronic acid. All of these molecular weights are values indicated on the purchased products. H200 is a hyaluronic acid with molecular weight of about 2,000,000 (HA-LQH, Kewpie Corporation), H80 is a hyaluronic acid with molecular weight of about 800,000 (FCH-80, Kikkoman Biochemifa Company), H10 is a hyaluronic acid with molecular weight of about 5 to 100,000 (FCH-SU, Kikkoman Biochemifa Company), H1 is a hyaluronic acid with molecular weight of about 10,000 (Hyalo-Oligo, Kewpie Corporation), and H0.2 is a hyaluronic acid with molecular weight of about 2,000 (Micro Hyaluronic Acid, Kikkoman Biochemifa Company).

In addition, glycerol (concentrated glycerin, MIYOSHI OIL & FAT CO., LTD.), citric acid (NACALAI TESQUE, INC.), vitamin C derivative (Apprecier, SHOWA DENKO K.K.), tocopherol (NACALAI TESQUE, INC.), adenosine (NACALAI TESQUE, INC.), polyethylene glycol (Polyethylene Glycol 400, Wako Pure Chemical Industries, Ltd.) were used. For all of other valuable components, grades described in Japanese Standards of Cosmetic Ingredients were used.

TABLE 1

| | | Hyaluronic acid | | | | | Glyc-erin | Acid | | | | | Valuable Component | | | Water |
|---|---|---|---|---|---|---|---|---|---|---|---|---|---|---|---|---|
| | | 2 million | 800,000 | 100,000 | 10,000 | 2000 | | Citric acid | Lactic acid | Tartaric acid | Hydrochloric acid | Acetic acid | Tocopherol | VC | Adenosine | |
| Examples | 1 | 1 | | | | | 1 | 0.2 | | | | | | | | 197.8 |
| | 2 | 1 | | | | | 5 | 0.2 | | | | | | | | 193.8 |
| | 3 | 1 | | | | | 20 | 0.2 | | | | | | | | 178.8 |
| | 4 | 1 | | | | | 40 | 0.2 | | | | | | | | 158.8 |
| | 5 | 1 | | | | | 60 | 0.2 | | | | | | | | 138.8 |
| | 6 | 1 | | | | | 80 | 0.2 | | | | | | | | 118.8 |
| | 7 | | 2 | | | | 20 | 0.4 | | | | | | | | 177.6 |
| | 8 | | 2 | | | | 60 | 0.4 | | | | | | | | 137.6 |
| | 9 | | | 10 | | | 20 | 4 | | | | | | | | 166 |
| | 10 | | | 10 | | | 60 | 4 | | | | | | | | 126 |
| | 11 | 0.5 | 0.5 | | | | 40 | 0.2 | | | | | | | | 158.8 |
| | 12 | 0.5 | | 0.5 | | | 40 | 0.2 | | | | | | | | 158.8 |
| | 13 | 1 | | | 0.1 | | 40 | 0.2 | | | | | | | | 158.7 |
| | 14 | 0.5 | | | 0.5 | | 40 | 0.2 | | | | | | | | 158.8 |
| | 15 | 1 | | | | 0.1 | 40 | 0.2 | | | | | 0.1 | | | 158.6 |
| | 16 | 0.5 | | | | 0.5 | 40 | 0.2 | | | | | | | 0.1 | 158.7 |
| | 17 | 0.5 | | | | 0.5 | 40 | 0.2 | | | | | | 0.1 | | 158.7 |
| | 18 | 1 | | | | | 40 | 0.1 | | | | | | | | 158.9 |
| | 19 | 1 | | | | | 40 | 0.2 | | | | | | | | 158.8 |
| | 20 | 1 | | | | | 40 | 0.5 | | | | | | | | 158.5 |
| | 21 | 1 | | | | | 40 | 1 | | | | | | | | 158 |
| | 22 | 1 | | | | | 40 | | 0.5 | | | | | | | 158.5 |
| | 23 | 1 | | | | | 40 | | | 0.1 | | | | | | 158.9 |
| Comparative Examples | 1 | 1 | | | | | 0.5 | 0.2 | | | | | | | | 198.3 |
| | 2 | 1 | | | | | 150 | 0.2 | | | | | | | | 48.8 |
| | 3 | | | 20 | | | 20 | 8 | | | | | | | | 152 |
| | 4 | | | | 20 | | 20 | 8 | | | | | | | | 152 |
| | 5 | 1 | | | | | 40 | 0.05 | | | | | | | | 158.9 |
| | 6 | 1 | | | | | 40 | | | | 0.1 | | | | | 158.9 |
| | 7 | 1 | | | | | 40 | | | | 1 | | | | | 158 |
| | 8 | 1 | | | | | 40 | | | | | 0.1 | | | | 158.9 |
| | 9 | 1 | | | | | 40 | | | | | 1 | | | | 158.9 |

Note:
VC: Vitamin C derivative

TABLE 2

| | | Hyaluronic acid | | | | | Polyhydric alcohol | | | | Citric acid | Water |
|---|---|---|---|---|---|---|---|---|---|---|---|---|
| | | 2 million | 800,000 | 100,000 | 10,000 | 2000 | Glycerin | Propylene | Polyethylene | Butylene | | |
| Examples | 24 | 1 | | | | | 20 | | | | 0.2 | 178.8 |
| | 25 | 1 | | | | | 40 | | | | 0.2 | 158.8 |
| | 26 | 1 | | | | | | | 10 | | 0.2 | 188.8 |
| | 27 | 1 | | | | | | | 20 | | 0.2 | 178.8 |
| | 28 | 1 | | | | | | | | 10 | 0.2 | 188.8 |
| | 29 | 1 | | | | | | | | 20 | 0.2 | 178.8 |

Note:
Propylene: propylene glycol,
Polyethylene: polyethylene glycol 400,
Butylene: butylene glycol Respective aqueous solutions, each of which contains the hyaluronic acid, the polyhydric alcohol, and the polycarboxylic acid or oxycarbonic acid, were stirred and homogenized by a propeller type rotary stirrer, for preparation. In Examples 15 and 16, the tocopherol and the adenosine were dissolved in a small amount of ethanol and then added. The prepared aqueous solution was applied on a polyethylene terephthalate film with a thickness of 26 μm (DIAFOIL #130-26: Mitsubishi Plastics, Inc.) so that the thickness was uniform, and dried at 80° C. by a geer type oven for 30 minutes to obtain a hyaluronic acid gel sheet with a thickness of about 200 μm or a non-gelatinized viscous material.

(Comparison of Properties Among the Produced Hyaluronic Acid Gel Sheets)

The produced hyaluronic acid gel sheets obtained in Examples 1 to 29 and Comparative Examples 1 to 9 were evaluated from the following three view points. The results of the evaluations are summarized in Table 3 below.

1. Results of Observation for the Properties

Results of observation for flexibility, elasticity and tensile strength by naked eye and sense of touch are shown.

2. Results of Test for Adherence to the Skin

Results of test for adherence to the skin in which hyaluronic acid gel sheets (2 cm×2 cm) were applied on insides of forearms of human volunteers are shown.

3. Solubility Test

Hyaluronic acid gel sheets (2 cm×2 cm) were applied on forearms of human volunteers, on which 10 ml of water was dripped, and the skin was massaged over the sheet for 3 minutes, and the solubility of the hyaluronic acid gel was observed.

TABLE 3

|  |  | Property | Adherence to skin | Solubility |
|---|---|---|---|---|
| Examples | 1 | A | A | A |
|  | 2 | A | A | A |
|  | 3 | A | A | A |
|  | 4 | A | A | A |
|  | 5 | A | A | A |
|  | 6 | A | A | A |
|  | 7 | A | A | A |
|  | 8 | A | A | A |
|  | 9 | A | A | A |
|  | 10 | A | A | A |
|  | 11 | A | A | A |
|  | 12 | A | A | A |
|  | 13 | A | A | A |
|  | 14 | A | A | A |
|  | 15 | A | A | A* |
|  | 16 | A | A | A* |
|  | 17 | A | A | A* |
|  | 18 | A | A | A |
|  | 19 | A | A | A |
|  | 20 | A | A | A |
|  | 21 | A | A | A |
|  | 22 | A | A | A |
|  | 23 | A | A | A |
|  | 24 | A | A | A |
|  | 25 | A | A | A |
|  | 26 | A | A | A |
|  | 27 | A | A | A |
|  | 28 | A | A | A |
|  | 29 | A | A | A |

TABLE 3-continued

|  |  | Property | Adherence to skin | Solubility |
|---|---|---|---|---|
| Comparative Examples | 1 | B | C | B |
|  | 2 | D | Insufficient sheet forming | Unable to test |
|  | 3 | D | Unable to form sheet | Unable to test |
|  | 4 | D | Unable to form sheet | Unable to test |
|  | 5 | D | Unable to form sheet | Unable to test |
|  | 6 | D | Unable to form sheet | Unable to test |
|  | 7 | D | Unable to form sheet | Unable to test |
|  | 8 | D | Unable to form sheet | Unable to test |
|  | 9 | D | Unable to form sheet | Unable to test |

Respective symbols in Table 3 mean the following results.

In the observation results for properties, A represents that all of flexibility, elasticity and tensile strength are sufficient, B represents that flexibility and elasticity are insufficient but tensile strength is sufficient, C represents that flexibility and elasticity are sufficient but tensile strength is insufficient, and D represents that it is a liquid, and all of flexibility, elasticity and tensile strength are insufficient.

In the skin adherence test, A represents good adherence, B represents adherence with partial detachment, and C represents no adherence and moreover detachment. Basically, the products showing C and D in the observation results for the properties were not the subjects for this test.

In the solubility test, A represents complete dissolution, and B represents partial dissolution. A* represents rapid dissolution within 30 seconds. Basically, the products showing C and D in the observation results for the properties were not the subjects for this test.

(Evaluation of Moisturizing Effects by an Application Test for the Hyaluronic Acid Gel Sheet)

The following four test samples were administered to the same sites of forearms of 5 human volunteers twice at morning and night for a total of 7 days, and one day after the completion of the administration (8 days after the start of the administration), their skin moisture contents were measured using Cutometer (MPA 580). The results of the measurement were indicated as electrostatic capacities (unit: a.u.). Also, their skin moisture contents before administration were measured as controls. The increment of electrostatic capacity (=increment of the moisture content) compared with that before administration were summarized in Table 4. The results are represented by an average and a standard deviation (SD) of the results of the 5 subjects.

TABLE 4

| Test Examples | Target Samples | Average and SD of increment of electrostatic capacity of skin (unit: a.u.) |
|---|---|---|
| 1 | Example 4 Gel sheet | 42 ± 6 |
| 2 | Example 17 Gel sheet | 47 ± 5 |
| 3 | Example 17 Solution | 49 ± 8 |
| 4 | WO01/57093 Example 6 | 30 ± 6 |

The test samples and the administration method were as below.

Test example 1: The hyaluronic acid gel sheet (2 cm×2 cm) in Example 4 was applied on the forearm for 30 minutes, then the skin was massaged while the gel was dissolved by adding about 10 mL of purified water on the gel little by little for about 3 minutes, then it was rinsed with purified water, and naturally dried.

Test example 2: The hyaluronic acid gel sheet (2 cm×2 cm) in Example 17 was applied on the forearm for 30 minutes, then the skin was massaged while the gel was dissolved by adding about 10 mL of purified water on the gel little by little for about 3 minutes, then it was rinsed with purified water, and naturally dried.

Test example 3: About 1 mL of the aqueous solution before preparation of the gel in Example 17 was applied on the forearm (about 2 cm×2 cm), and 30 minutes later, the skin was massaged for about 3 minutes, then it was rinsed with purified water, and naturally dried.

Test example 4: According to the method described in Example 6 of WO01/57093, the hyaluronic acid gel sheet (2 cm×2 cm) prepared using an aqueous solution containing 0.5% of hyaluronic acid (HA-LQH: Kewpie Corporation) and 0.5% of hyaluronic acid (Hyalo-Oligo: Kewpie Corporation) was applied on the forearm for 30 minutes, then the skin was massaged while adding about 10 mL of purified water on the gel little by little for about 10 minutes, then it was rinsed with purified water, and naturally dried.

The hyaluronic acid gel sheet showed significant increase of the skin moisture content compared to Example 6 in WO01/57093. In addition, the hyaluronic acid gel sheets in Examples 4 and 17 showed increment of the skin moisture content equal to that in the aqueous solution before preparation of the gel in Example 17. Furthermore, in sensory evaluation in all of 5 human volunteers, the hyaluronic acid gel sheets in Examples 4 and 17 showed handleability and sense of use in its administration to the skin superior to those of the hyaluronic acid aqueous solution in Example 17.

(Evaluation for the Provision of Warm Sensation and $CO_2$ Gas-generating Effects by Application Test of the Hyaluronic Acid Gel Sheet)

The hyaluronic acid gel sheets in Examples 30 to 36 were produced according to the compounding ratios (weight ratio) described in Table 5 below. Aqueous solutions of each constituent were stirred and homogenized by a propeller type rotary stirrer, for preparation. The prepared aqueous solution was applied on a polyethylene terephthalate film with a thickness of 26 μm (DIAFOIL #130-26: Mitsubishi Plastics, Inc.) so that the thickness was uniform, and dried at 80° C. by a geer type oven for 30 minutes to obtain a hyaluronic acid gel sheet with a thickness of about 200 μm. This hyaluronic acid gel sheet was cut to obtain a circle hyaluronic acid gel sheet with a diameter of 20 cm, and a face mask having holes corresponding to eyes and mouth was produced.

Also, the hyaluronic acid gel sheets in Comparative Examples 10 and 11 were similarly produced according to the compounding ratios (weight ratio) described in Table 5. Also, their face masks were similarly produced. The thicknesses of the films for the hyaluronic acid gel sheets were 15 μm and 25 μm respectively.

TABLE 5

| | | Hyaluronic acid | | Polyhydric alcohol | | Acid | | | Valuable Component |
| --- | --- | --- | --- | --- | --- | --- | --- | --- | --- |
| | | 2 million | 2000 | Glycerin | Polyethylene | Lactic acid | Citric acid | Tartaric acid | Collagen |
| Examples | 30 | 1 | 0.1 | 30 | 5 | 0.2 | 0.6 | 0.2 | 1 |
| | 31 | 1 | 0.1 | 40 | 0 | 0.2 | 0.8 | 0 | 2 |
| | 32 | 1 | 0.1 | 60 | 0 | 0 | 1 | 0 | 0 |
| | 33 | 1 | 0 | 50 | 0 | 0 | 0 | 1 | 0 |
| | 34 | 1 | 0.1 | 40 | 0 | 0.2 | 0.6 | 0.2 | 1 |
| | 35 | 1 | 0 | 40 | 2 | 0.2 | 0.8 | 0 | 2 |
| | 36 | 1 | 0.1 | 50 | 0 | 0 | 0.2 | 0.8 | 0 |
| Comparative Examples | 10 | 1 | 0 | 50 | 0 | 0.2 | 0.6 | 0.2 | 0 |
| | 11 | 1 | 0.05 | 50 | 2 | 0.2 | 0.6 | 0 | 0 |

| | | Valuable Component | | | | | | | |
| --- | --- | --- | --- | --- | --- | --- | --- | --- | --- |
| | | Acetyl-glucosamine | Trehalose | Niacinamide | Glycyrrhizin 2K | Adenosine | Scutellaria | Hydroxy | Water |
| Examples | 30 | 0 | 0 | 0.02 | 0.01 | 0.05 | 0.02 | 0 | 150 |
| | 31 | 0 | 0 | 0.02 | 0.01 | 0.05 | 0.02 | 0 | 150 |
| | 32 | 1 | 0 | 0.02 | 0.01 | 0.1 | 0.02 | 0.1 | 150 |
| | 33 | 1 | 0 | 0.02 | 0.01 | 0.05 | 0.02 | 0.1 | 150 |
| | 34 | 0 | 0 | 0.02 | 0.01 | 0.05 | 0.02 | 0 | 150 |
| | 35 | 0 | 0 | 0.02 | 0.01 | 0.05 | 0.02 | 0 | 150 |
| | 36 | 1 | 0 | 0.02 | 0.01 | 0.1 | 0.02 | 0 | 150 |
| Comparative Examples | 10 | 1 | 0 | 0.02 | 0.01 | 0.05 | 0.02 | 0 | 150 |
| | 11 | 0 | 1 | 0.02 | 0.01 | 0.1 | 0.02 | 0 | 150 |

Note:
Polyethylene: polyethylene glycol 400,
Scutellaria: scutellaria baiealensis extract,
Hydroxy: hydroxypropyl-cellulose The skin lotion for the test was produced according to the compounding ratios (weight ratio) for the components described in Table 6 below. Aqueous solutions of each constituent were mixed by a propeller type rotary stirrer, for preparation.

TABLE 6

| Skin lotion | Hyaluronic acid 2000 | Acetyl-glucosamine | Scutellaria baicalensis extract | Butylene glycol | Glycerin | Oleyl alcohol | POE (25) | Methyl paraben | Sodium bicarbonate | Water |
|---|---|---|---|---|---|---|---|---|---|---|
| A | 0.01 | 1 | 0.01 | 6 | 4 | 0.1 | 0.5 | 0.05 | 1 | 85 |
| B | 0.01 | 1 | 0.01 | 6 | 4 | 0.1 | 0.5 | 0.05 | 0 | 85 |

Each of the obtained face masks was applied on the face of the volunteer lying face up, and presence of warm sensation at the application site on the skin was evaluated. The skin temperatures at the application site and the non-application site were measured to calculate the temperature difference between them. For measurement of the skin temperature, a digital thermometer (GT-07) was used.

Subsequently, about 0.5 mL of skin lotion for the test was sprayed to the whole surface of the face mask by a spray, and the skin was massaged to evaluate foaming of $CO_2$ gas. In this test, skin lotion A was used in Examples 30 to 35 and Comparative Examples 10 and 11, and skin lotion B was used in Example 36.

The evaluation results were summarized in Table 7 below. The face mask was dissolved by massage for about 3 minutes, then it was rinsed with purified water, and naturally dried.

TABLE 7

| | | Handle-abiliy | Test result for warm sensation of skin | Test result for $CO_2$ gas foaming |
|---|---|---|---|---|
| Examples | 30 | Good | Skin temperature increased by 0.5° C. for more than 1 min | Intense foaming |
| | 31 | " | Skin temperature increased by 0.5° C. for more than 1 min | Intense foaming |
| | 32 | " | Skin temperature increased by 0.5° C. for more than 1 min | Intense foaming |
| | 33 | " | Skin temperature increased by 0.5° C. for more than 1 min | Intense foaming |
| | 34 | " | Skin temperature increased by 0.5° C. for more than 1 min | Intense foaming |
| | 35 | " | Skin temperature increased by 0.5° C. for more than 1 min | Intense foaming |
| | 36 | " | Skin temperature increased by 0.5° C. for more than 1 min | No foaming |
| Comparative Examples | 10 | Insufficient sheet strength, difficult to handle | Skin temperature increased by 0.3° C. or less | Small amount of foam generated |
| | 11 | Insufficient sheet strength, difficult to handle | Skin temperature increased by 0.3° C. or less | Small amount of foam generated |

The invention claimed is:

1. A hyaluronic acid gel sheet comprising hyaluronic acid alcogel containing 100 parts by weight of a hyaluronic acid having a molecular weight of from $5 \times 10^4$ to $5 \times 10^6$ daltons, 10 to 100 parts by weight of polycarboxylic acid or oxycarbonic acid, and 100 to 8000 parts by weight of polyhydric alcohol, wherein a thickness of the sheet is in a range of 30 µm to 1 mm, wherein the polyhydric alcohol is selected from the group consisting of glycerin, propylene glycol, ethylene glycol, polyethylene glycol, 1,3-butylene glycol, dipropylene glycol and sorbitol, and wherein the hyaluronic acid alcogel is formed by drying an aqueous solution containing the hyaluronic acid, the polycarboxylic acid or oxycarbonic acid, and the polyhydric alcohol to remove water therefrom.

2. The hyaluronic acid gel sheet according to claim 1, wherein the hyaluronic acid alcogel further comprises:

10 parts by weight or more of a hyaluronic acid whose molecular weight is $2 \times 10^4$ daltons or below in addition to the 100 parts by weight of said hyaluronic acid having a molecular weight of from $5 \times 10^4$ to $5 \times 10^6$ daltons.

3. The hyaluronic acid gel sheet according to claim 1, wherein the polycarboxylic acid or oxycarbonic acid is at least one or more carboxylic acids selected from a group consisting of citric acid, tartaric acid and lactic acid.

4. The hyaluronic acid gel sheet according to claim 1, wherein the polyhydric alcohol is glycerin.

5. The hyaluronic acid gel sheet according to claim 1, further containing at least one or more compounds selected from a group consisting of hydroxypropyl cellulose, polyvinylpyrrolidone, polyvinyl alcohol, carboxymethylcellulose, polyacrylic acid and polyethylene glycol.

6. The hyaluronic acid gel sheet according to claim 1, further containing active ingredients used for cosmetics and medicinal products.

7. A method for manufacturing a hyaluronic acid gel sheet, including a step of preparing an aqueous solution by uniformly dissolving 100 parts by weight of a hyaluronic acid, having a molecular weight of from $5 \times 10^4$ to $5 \times 10^6$ daltons, 10 to 100 parts by weight of a polycarboxylic acid or oxycarbonic acid and 100 to 8000 parts by weight of a polyhydric alcohol in water, and a step of producing the hyaluronic acid gel sheet by applying the aqueous solution on a film so that its thickness is uniform and drying it to remove water therefrom, wherein the polyhydric alcohol is selected from the group consisting of glycerin, propylene glycol, ethylene glycol, polyethylene glycol, 1,3-butylene glycol, dipropylene glycol and sorbitol.

8. The hyaluronic acid gel sheet according to claim 2, wherein the polycarboxylic acid or oxycarbonic acid is at least one or more carboxylic acids selected from a group consisting of citric acid, tartaric acid and lactic acid.

9. The hyaluronic acid gel sheet according to claim 2, wherein
the polyhydric alcohol is glycerin.

10. The hyaluronic acid gel sheet according to claim 3, wherein
the polyhydric alcohol is glycerin.

11. The hyaluronic acid gel sheet according to claim 2, further containing at least one or more compounds selected from a group consisting of hydroxypropyl cellulose, polyvinylpyrrolidone, polyvinyl alcohol, carboxymethylcellulose, polyacrylic acid and polyethylene glycol.

12. The hyaluronic acid gel sheet according to claim 3, further containing at least one or more compounds selected from a group consisting of hydroxypropyl cellulose, polyvinylpyrrolidone, polyvinyl alcohol, carboxymethylcellulose, polyacrylic acid and polyethylene glycol.

13. The hyaluronic acid gel sheet according to claim 4, further containing at least one or more compounds selected from a group consisting of hydroxypropyl cellulose, polyvinylpyrrolidone, polyvinyl alcohol, carboxymethylcellulose, polyacrylic acid and polyethylene glycol.

14. The hyaluronic acid gel sheet according to claim 2, further containing active ingredients used for cosmetics and medicinal products.

15. The hyaluronic acid gel sheet according to claim 3, further containing active ingredients used for cosmetics and medicinal products.

16. The hyaluronic acid gel sheet according to claim 4, further containing active ingredients used for cosmetics and medicinal products.

17. The hyaluronic acid gel sheet according to claim 5, further containing active ingredients used for cosmetics and medicinal products.

18. A hyaluronic acid gel sheet comprising hyaluronic acid alcogel containing 100 parts by weight of a hyaluronic acid having a molecular weight of from $5\times10^4$ to $5\times10^6$ daltons, 10 parts by weight or more of a hyaluronic acid having a molecular weight of $2\times10^4$ daltons or below, 10 to 100 parts by weight of polycarboxylic acid or oxycarbonic acid, and 100 to 8000 parts by weight of polyhydric alcohol, wherein a thickness of the sheet is in a range of 30 μm to 1 mm.

19. A method for manufacturing a hyaluronic acid gel sheet, including
a step of preparing an aqueous solution uniformly dissolving 100 parts by weight of a hyaluronic acid having a molecular weight of from $5\times10^4$ to $5\times10^6$ daltons, 10 parts by weight or more of a hyaluronic acid having a molecular weight of $2\times10^4$ daltons or below, 10 to 100 parts by weight of a polycarboxylic acid or oxycarbonic acid and 100 to 8000 parts by weight of a polyhydric alcohol in water, and
a step of producing the hyaluronic acid gel sheet by applying the aqueous solution on a film so that its thickness is uniform and drying it.

20. The method for manufacturing a hyaluronic gel sheet according to claim 7, farther comprising:
dissolving an active ingredient used for cosmetics and medicinal products in ethanol and then adding it to the prepared aqueous solution prior to producing the hyaluronic acid gel sheet.

21. The hyaluronic acid gel sheet according to claim 1, wherein the hyaluronic acid alcogel further comprises:
10 to 100 parts by weight of a hyaluronic acid whose molecular weight is $2\times10^4$ daltons or below in addition to the 100 parts by weight of said hyaluronic acid having a molecular weight of from $5\times10^4$ to $5\times10^6$ daltons.

* * * * *